United States Patent
Adachi et al.

[11] Patent Number: 5,948,917
[45] Date of Patent: Sep. 7, 1999

[54] 3-(ISOXAZOL-5-YL)-SUBSTITUTED BENZOIC ACID DERIVATIVE AND METHOD FOR PRODUCTION THEREOF

[75] Inventors: Hiroyuki Adachi, Odawara; Masao Yamaguchi, Hiratsuka; Osamu Miyahara, Odawara; Takahiro Sagae, Oiso-machi, all of Japan

[73] Assignee: Nippon Soda Co., Ltd., Tokyo, Japan

[21] Appl. No.: 08/875,548

[22] PCT Filed: Feb. 10, 1997

[86] PCT No.: PCT/JP97/00341

§ 371 Date: Oct. 2, 1997

§ 102(e) Date: Oct. 2, 1997

[87] PCT Pub. No.: WO97/35850

PCT Pub. Date: Oct. 2, 1997

[30] Foreign Application Priority Data

Mar. 26, 1996 [JP] Japan ................................. 8-096077

[51] Int. Cl.$^6$ .................................................. C07D 261/08
[52] U.S. Cl. ............................................................. 548/247
[58] Field of Search .............................................. 548/247

[56] References Cited

FOREIGN PATENT DOCUMENTS

| WO 96/26192 | 2/1996 | WIPO | 548/247 |
|---|---|---|---|
| WO 96/26193 | 2/1996 | WIPO | 548/247 |
| WO 96/26205 | 2/1996 | WIPO | 548/247 |
| WO 96/26206 | 2/1996 | WIPO | 548/247 |

*Primary Examiner*—Joseph K. McKane
*Attorney, Agent, or Firm*—Joseph C. Mason, Jr.; Dennis G. LaPointe

[57] ABSTRACT

This invention concerns a benzoic acid represented by the formula [I]

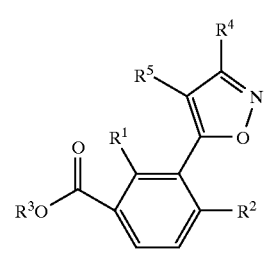

or a benzoic acid derivative and a method for the production of a compound represented by the formula [I]. The compound represented by the formula [I] is an intermediate for the production of a herbicidally active pyrazole compound represented by the formula [B]

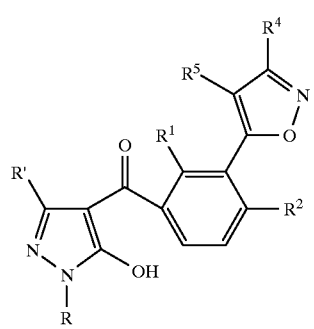

15 Claims, No Drawings

3-(ISOXAZOL-5-YL)-SUBSTITUTED BENZOIC ACID DERIVATIVE AND METHOD FOR PRODUCTION THEREOF

This application is a 371 of PCT/JP97/00341 filed Feb. 10, 1997.

TECHNICAL FIELD

This invention relates to a novel benzoic acid derivative which has a 1,2-isoxazol-5-yl group as a substituent at the 3 position of a benzene ring and a method for the production thereof.

BACKGROUND ART

As a pyrazole compound having a heterocycle substituted at the 3 position of a benzoyl moiety, the official gazette of WO96/26206 discloses a compound represented by the formula [A]

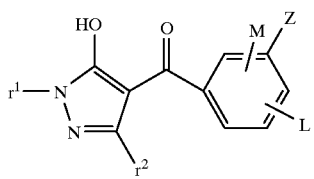

(wherein $r^1$ and $r^2$ each represent a hydrogen atom, a $C_{1-4}$ group, etc., M and L each represent a hydrogen atom, a halogen atom, a $C_{1-4}$ alkylsulfonyl group, etc., and Z represents a heteroyl group).

A general method for the production of those of the benzoic acid derivatives which possess a 1,2-isoxazol-5-yl group at the 3 position of a benzene ring, represented by the following formulas (a) and (b).

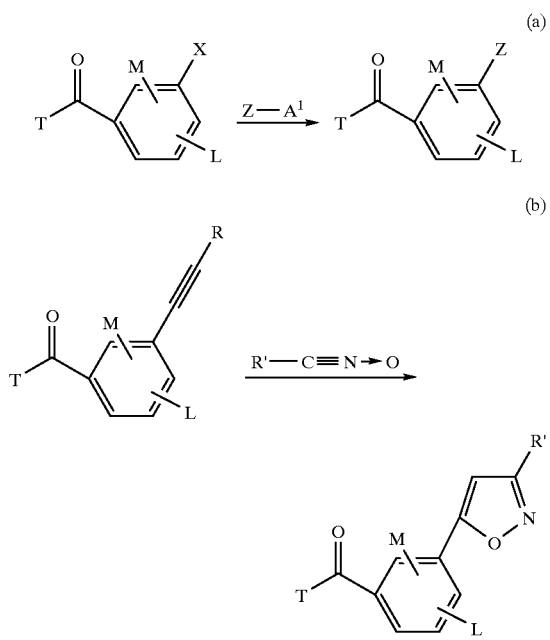

[wherein T represents a $C_{1-4}$ alkoxy group, L and M each represent a hydrogen atom, a $C_{1-4}$ alkyl group, a halogen atom, an alkylsulfonyl group, etc. X represents Cl, Br, I, $OSO_2CF_3$, etc., $A_1$ represents an $Sn(C_{1-4}$ alkyl$)_3$, etc., Z represents a heteroyl group, R represents a hydrogen atom or a trimethyl silyl group, and R' represents a hydrogen atom or a $C_{1-4}$ alkyl group].

The actual synthesis of 3-(3-isopropylisoxazol-5-yl)-4-methylsulfonyl benzoic acid by the method of production (b) has been reported.

No concrete example of the synthesis of 2,4-di-substituted-3-(1,2-isoxazol-5-yl)benzoic acids according to this invention, however, has been reported to the art.

DISCLOSURE OF THE INVENTION

This invention has for an object thereof the provision of 2-4-di-substituted-3-(1,2-isoxazol-5-yl) benzoic acid derivatives which are intermediates for the production of selective herbicides and a commercially advantageous method for the production thereof.

The present inventors have found that the pyrazole compounds represented by the formula [B]

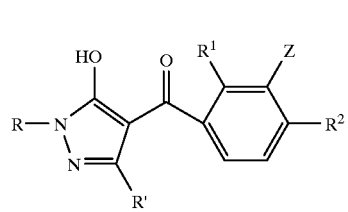

(wherein R and R' each represent a hydrogen atom or a $C_{1-6}$ alkyl group, $R^1$ represents a halogen atom, a $C_{1-6}$ alkyl group, a $C_{1-6}$ alkoxy group, a $C_{1-6}$ haloalkyl group, or a $C_{1-6}$ haloalkoxy group, $R^2$ represents a halogen atom, a $C_{1-6}$ alkyl group, a $C_{1-6}$ alkoxy group, a $C_{1-6}$ haloalkyl group, a $C_{1-6}$ haloalkoxy group, a $C_{1-6}$ alkoxythio group, or a $C_{1-6}$ alkylsulfonyl group, and Z represents an optionally substituted 1,2-isoxazol-5-yl group) possess veritably excellent herbicidal activity, crop selectivity, and selectivity particularly for wheat and corn as compared with compounds of other 3-heterocyclic groups.

They have further found a commercially advantageous method for the production of 2,4-di-substituted-3-(1,2-isoxazol-5-yl) benzoic acid derivatives constituting intermediates for the production of the pyrazole compounds mentioned above. This invention has been perfected as a result.

Now, this invention will be described in detail below.

This invention concerns a benzoic acid derivative having a 1,2-isoxazol-5-yl group as a substituent at the 3 position of a benzoyl moiety represented by the formula [1]

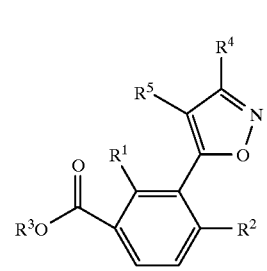

(wherein $R^1$ represents a halogen atom such as fluorine, chlorine, or bromine, a $C_{1-6}$ alkyl group such as methyl or ethyl group, a $C_{1-6}$ alkoxy group such as methoxy or ethoxy group, a $C_{1-6}$ haloalkyl group such as trifluoromethyl group, or a $C_{1-6}$ haloalkoxy group such as trifluoromethoxy group, $R^2$ represents a halogen atom such as fluorine, chlorine, or bromine, a $C_{1-6}$ alkyl group such as methyl or ethyl group, a $C_{1-6}$ alkoxy group such as methoxy or ethoxy group, a $C_{1-6}$ haloalkyl group such as trifluoromethyl group, a $C_{1-6}$ haloalkoxy group such as trifluoromethoxy group, a $C_{1-6}$ alkylthio group such as methylthio, ethylthio, propylthio, or isopropylthio group, a $C_{1-6}$ alkylsulfinyl group such as methyl-sulfinyl or ethylsulfinyl group, or a $C_{1-6}$ alkylsulfonyl group such as methylsulfonyl or ethylsulfonyl group, $R^3$ represents a hydrogen atom or a $C_{1-6}$ alkyl group such as methyl or ethyl group, and $R^4$ and $R^5$ independently represent a hydrogen atom or a $C_{1-6}$ alkyl group such as methyl or ethyl group).

This invention also concerns a method for the production of a benzoic acid derivative having a 1,2-isoxazol-5-yl group as a substituent at the 3 position of a benzoyl moiety represented by the formula [1] mentioned above.

The benzoic ester represented by the formula [I] which is the compound of this invention can be produced through any of the following routes.

(1) Method of production 1

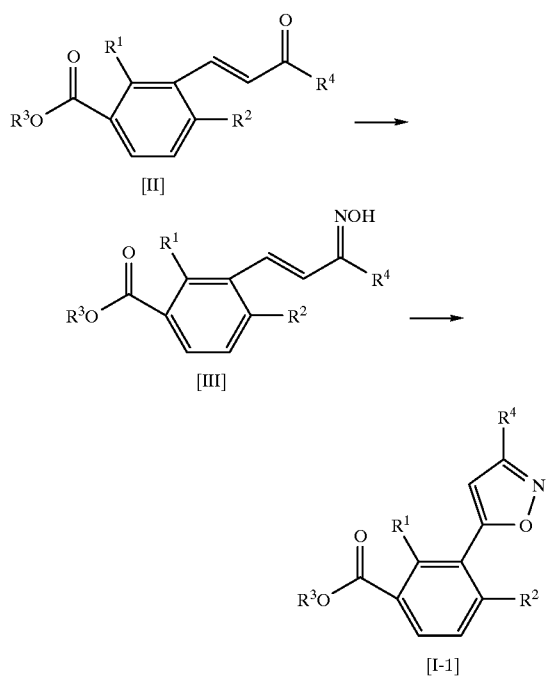

(wherein $R^1$, $R^2$, $R^3$, and $R^4$ have the same meanings as defined above).

Specifically, this method effects production of a benzoic ester represented by the formula [I-1] by causing hydroxy amine or a hydroxy amine salt to react on a compound represented by the formula [II] thereby converting the compound into a compound represented by the formula [III] and closing the open ring remaining therein.

(2) Method of production 2

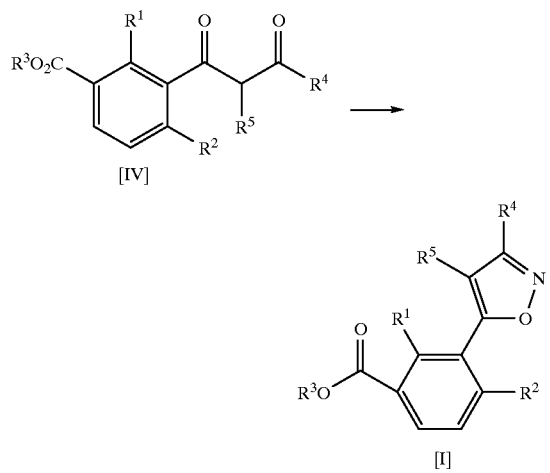

(wherein $R^1$, $R^2$, $R^3$, $R^4$, and $R^5$ have the same meanings as defined above).

Specifically, this method effects production of a benzoic ester represented by the formula [I-2] by causing hydroxy amine or a hydroxy amine salt to react on a compound represented by the formula [IV].

(3) Method of production 3

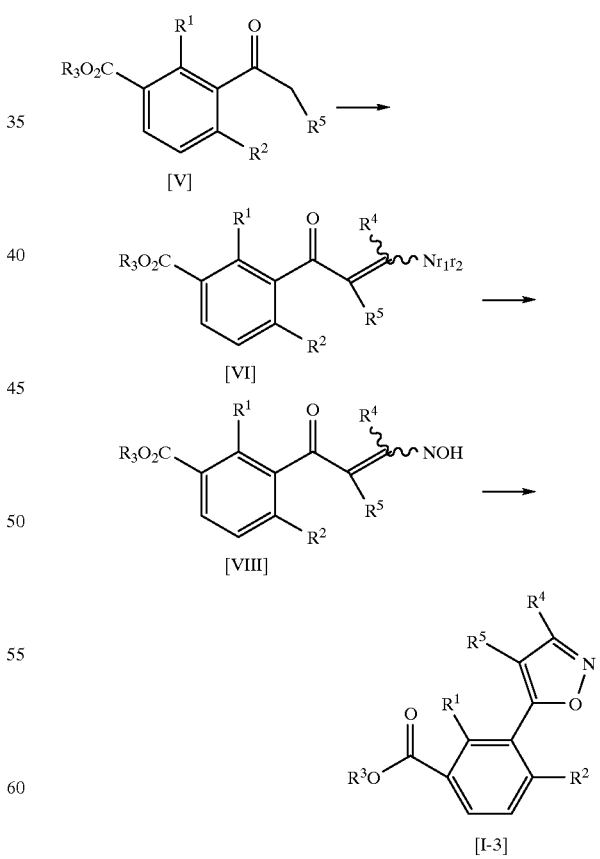

(wherein $R^1$, $R^2$, $R^3$, $R^4$, and $R^5$ have the same meanings as defined above and $r_1$ and $r_2$ each represent a lower alkyl group).

Specifically, this method effects production of a benzoic ester represented by the formula [I-3] by causing a N,N-dialkyl-alkylamide dialkyl acetal to react on a compound represented by the formula [V] thereby converting the compound into a compound represented by the formula [VI] and then causing hydroxy amine or a hydroxy amine salt to react on the compound thereby forming an intermediate represented by the formula [VIII] and closing the open ring remaining therein.

(wherein $R^1$, $R^2$, $R^3$, $R^4$, $R^5$ and $R^6$ have the same meanings as defined above).

Specifically, this method effects production of a benzoic ester represented by the formula [I-6] by causing a mercaptan represented by $R^6SH$ to react on a compound represented by the formula [I-4] in the presence of a base thereby converting this compound into a compound represented by the formula [I-5] and then oxidizing this compound.

An aldehyde compound (3) and a carboxylic acid compound (4) which are intermediates for the synthesis of the compound of this invention can be produced as follows.

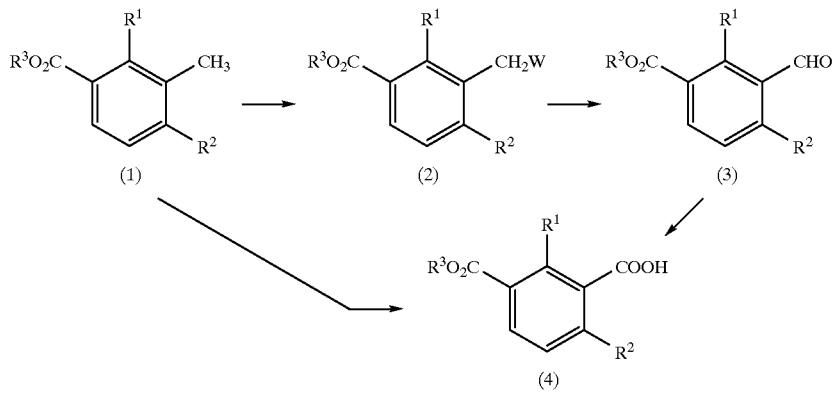

(4) Method of production 4

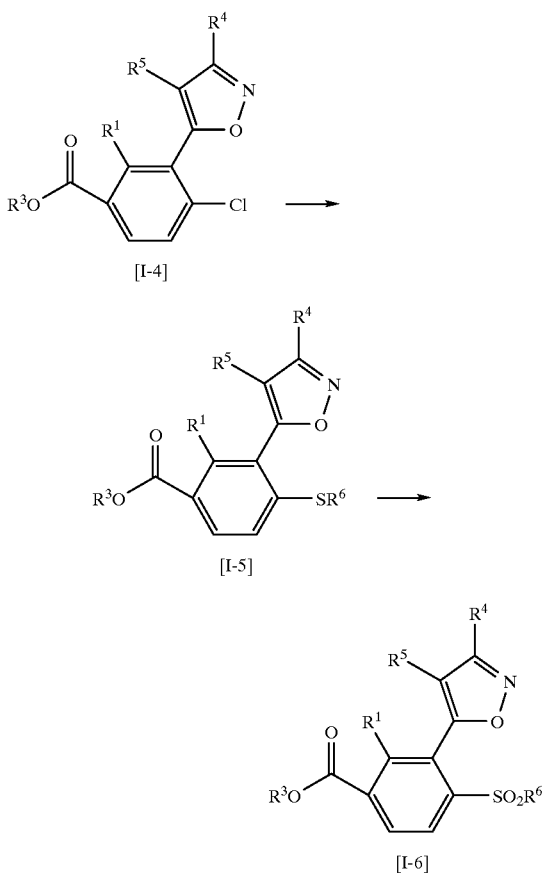

(wherein $R^1$ and $R^2$ have the same meanings as defined above, $R^3$ represents a hydrogen atom or a lower alkyl group, and W represents a halogen atom).

From the benzoic ester obtained as described above, a corresponding benzoic acid can be obtained by hydrolysis.

Specifically, from a toluene derivative (1), a benzyl halide derivative (2) is obtained by a well-known method, i.e. by causing a halogen such as chlorine or bromine or a halogenating agent such as N-bromosuccinic acid imide (NBS) or N-chloro-succinic acid imide (NCS) to react with the toluene derivative (1) in the presence of light or a radical reaction initiator such as benzoyl peroxide. Then, from the benzyl halide derivative (2), an aldehyde compound (3) can be derived by the method reported in J. Am. Chem. Soc., 71, 1767 (1949). Specifically, the aldehyde compound (3) is produced by causing an alkali metal salt of a nitro alkane such as 2-nitropropane to react in an alcohol solvent such as methanol or ethanol at a temperature between 0° C. and the boiling point of the solvent.

A carboxylic acid compound (4) can be produced by any of well-known methods, i.e. from the toluene derivative (1) by the oxidation reaction using potassium, permanganate or oxygen gas in the presence of a metal catalyst (as disclosed by JP-A-02-174,746, for example), or from the aldehyde compound (3) by the oxidation reaction using an oxidizing agent such as a Jones reagent, chromic acid or potassium permanganate.

Further, such various intermediates for synthesis as shown below can be derived from the aldehyde compound (3) and the carboxylic acid compound (4).

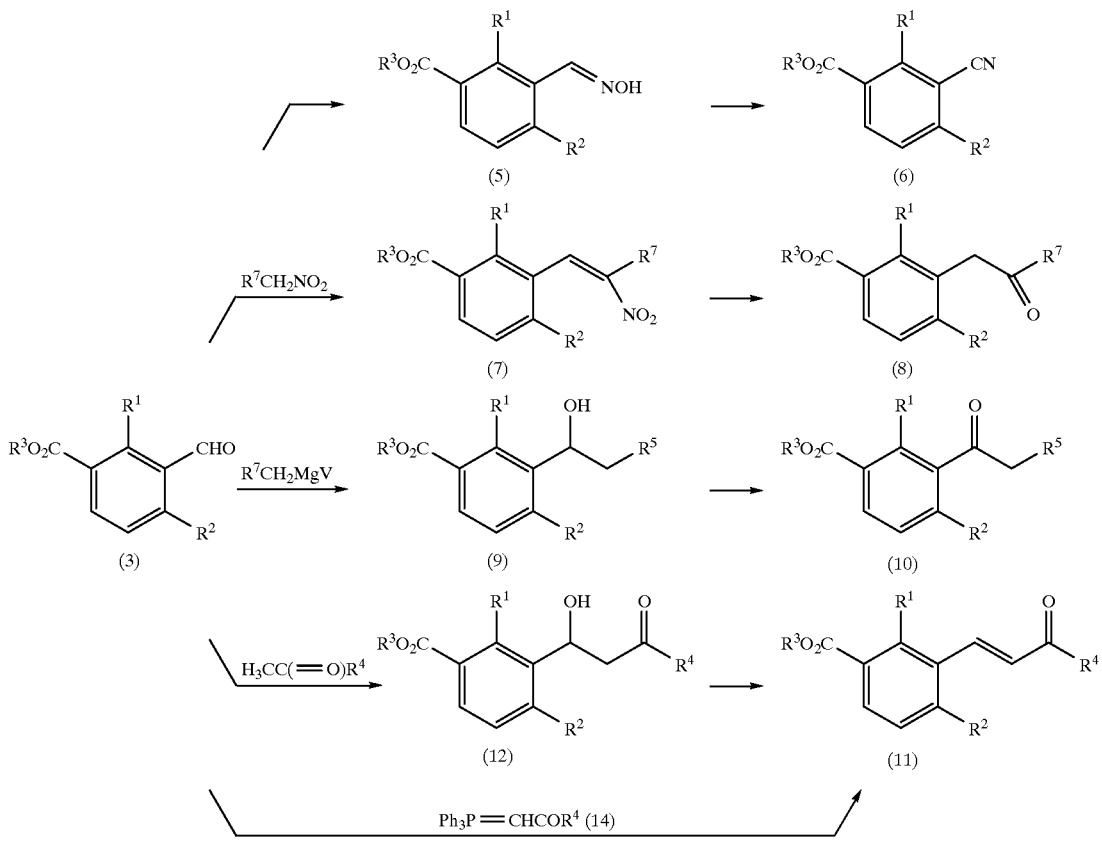

(wherein $R^1$, $R^2$, $R^3$, $R^4$, and $R^5$ have the same meanings as defined above, $R^7$ represents a lower alkyl group, and V represents a halogen atom).

An aldoxime compound (5) can be produced by causing the aldehyde (3) to react with a hydroxyl amine hydroxide or a hydroxyl amine sulfate in the presence of a base. Further, a cyano compound (6) can be produced by causing this aldoxime compound (5) to react with a dehydrating agent such as acetic anhydride, phosphorus pentoxide, or thionyl chloride.

Then, a ketone compound (8) can be produced by preparing a nitro olefin compound (7) by the application of the Knoevenagel condensation reaction reported as in Organic Reactions., 15, page 254, reducing this nitro olefin compound (7) with an activated iron-water system or lithium aluminum hydride, and then hydrolyzing the resultant product of reduction.

An acyl compound (10) can be produced by causing a Grignard reagent to react with the aldehyde compound (3) thereby preparing an alcohol compound (9) and oxidizing this alcohol compound (9) as with activated manganese dioxide or chromic acid.

A vinyl ketone compound (11) can be produced in accordance with a method well known from literature, i.e. by causing the aldehyde compound (3) to react with methyl ketone (13) in the presence of a catalyst in water, an organic solvent such as methylene chloride, chloroform, benzene, or toluene or a two-phase system of water with methylene chloride, chloroform, benzene, or toluene at a temperature in the range between 0° C. and the boiling point of the solvent to be used for a period of 1–50 hours thereby forming an aldol compound (12) and dehydrating this aldol compound (12) in a proper solvent in the presence of a catalyst. As concrete examples of the catalyst to be used in the reaction for the production of the aldol compound (12), metal hydroxides such as sodium hydroxide or barium hydroxide and organic bases such as piperidine or pyridine may be cited. As concrete examples of the catalyst to be used in the dehydration reaction, acids such as concentrated sulfuric acid or p-toluene sulfonic acid may be cited. As concrete examples of the solvent for the dehydration reaction, hydrocarbons such as benzene or toluene and halogenated hydrocarbons such as dichloromethane or chloroform may be cited.

The vinyl ketone compound (11) can be also produced by causing the aldehyde compound (3) to react with a phosphoran (14) in a proper solvent at a temperature between room temperature and the boiling point of the solvent to be used for a period from 10 minutes to 30 hours.

A β-diketone compound (15) can be produced as follows.

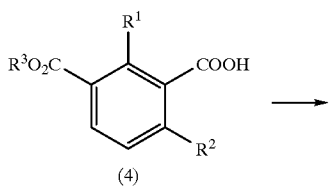

(4)

-continued

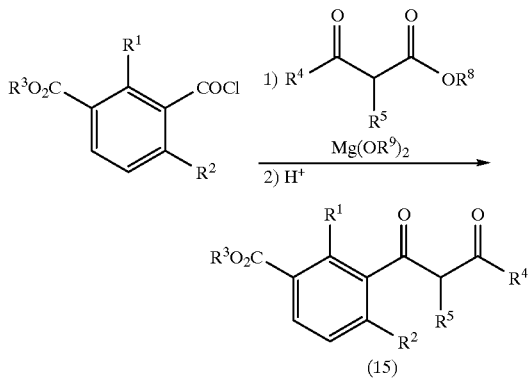

(wherein $R^1$, $R^2$, $R^3$, $R^4$, and $R^5$ have the same meanings as defined above and $R^8$ and $R^9$ each represent a lower alkyl group).

Specifically, a carbonyl chloride compound (16) can be produced by causing the carboxylic acid compound (4) to react with a chlorinating agent such as phosgene, thionyl chloride, or oxalyl chloride in an inert solvent such as a hydrocarbon like benzene or toluene or a halogenated hydrocarbon like methylene chloride or chloroform. Then, the β-diketone compound (15) can be produced by causing the carbonyl chloride compound (16) to react with a magnesium salt obtained from a β-keto ester (17) and magnesium alcoholate in accordance with a well-known method.

Now, the method for the synthesis of the compound of this invention will be described in detail below.

The compound of this invention can be produced by any of the methods of production shown below.

(1) Method of production 1

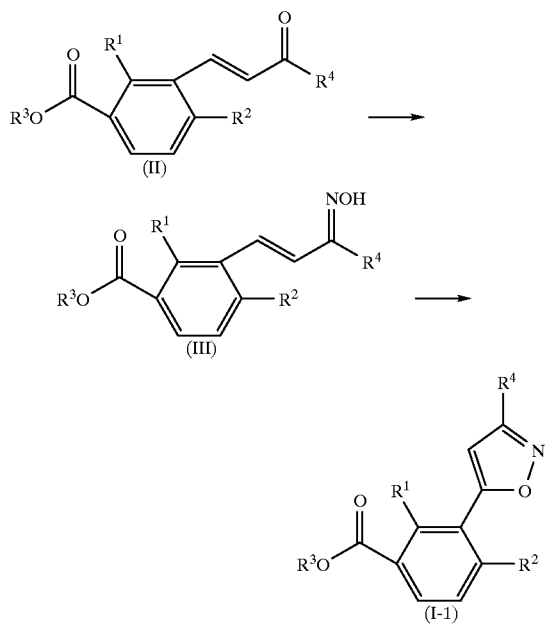

(wherein $R^1$, $R^2$, $R^3$, and $R^4$ have the same meanings as defined above).

The isoxazole compound [I-1] can be produced by causing the vinyl ketone compound [II] to react with hydroxyl amine in a proper solvent at a temperature between 0° C. and the oiling point of the solvent to be used for a period of 0.5–30 hours thereby obtaining the oxime compound [III] and further performing a ring-closing oxidizing reaction thereon. The hydroxyl amine to be used for the oximation reaction is in the form of a sulfate or hydrochloride. The reaction may be carried out without being neutralized or it may be performed after being neutralized with a proper base. As concrete examples of the base used for the neutralization, carbonates such as sodium hydrogen carbonate and potassium carbonate, alkali metal hydroxides such as sodium hydroxide and potassium hydroxide, carboxylates such as sodium acetate, metal alcoholates such as sodium methylate and sodium ethylate, and organic bases such as triethyl amine and pyridine may be cited. As concrete examples of the solvent to be used for this neutralization, alcohols such as methanol, ethanol, and isopropanol, hydrocarbons such as benzene and toluene, halogenated hydrocarbons such as dichloromethane and chloroform, ethers such as THF and dioxane, nitrites such as acetonitrile, DMF, pyridine, acetic acid, water, and mixed solvents of two or more of these solvents may be cited. For the ring-closing oxidizing reaction, an iodine-potassium, N-bromosuccinimide, or palladium catalyst system is used which is produced in accordance with the method disclosed respectively in J. Amer. Chem. Soc., 94, 9128, (1972); J. Heterocycl. Chem. 14, 1289 (1977); or Tetrahydron Lett. 1973, 5075.

(2) Method of production 2

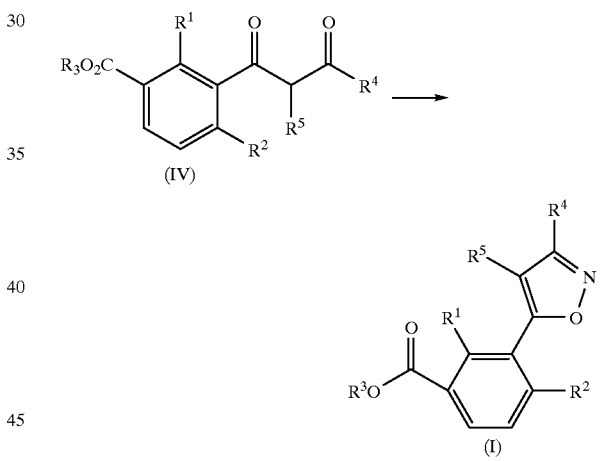

(wherein $R^1$, $R^2$, $R^3$, $R^4$, and $R^5$ have the same meanings as defined above).

The isoxazole compound represented by the general formula [I] can be alternatively produced by the reaction of a diketone compound [IV] with hydroxyl amine. The hydroxyl amine can be used in the form of a hydrochloride or a sulfate. This reaction proceeds smoothly in a proper solvent at a temperature between 0° C. and the boiling point of the solvent to be used. In this reaction, an acid such as sulfuric acid or p-toluene sulfonic acid can be used as a catalyst. As concrete examples of the solvent to be used for this reaction, alcohols such as methanol, ethanol, and isopropanol, hydrocarbons such as benzene and toluene, halogenated hydrocarbons such as dichloromethane and chloroform, ethers such as THF and dioxane, nitriles such as acetonitrile, DMF, pyridine, acetic acid, water, and mixed solvents of two or more of these solvents may be cited.

(3) Method of production 3

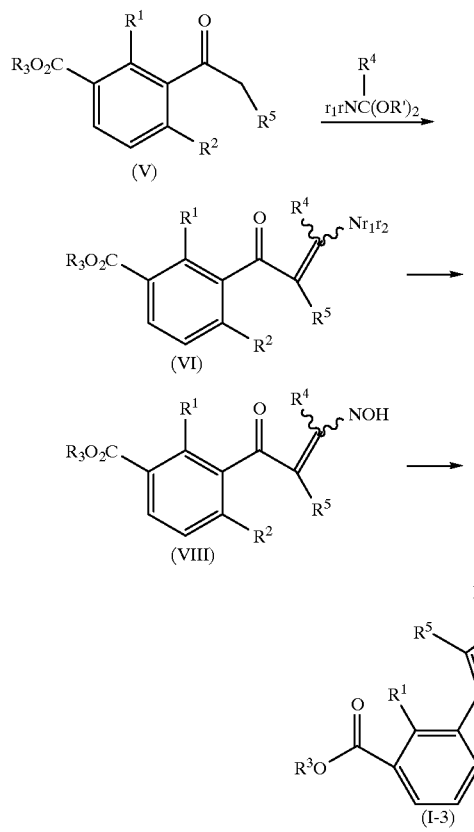

(4) Method of production 4

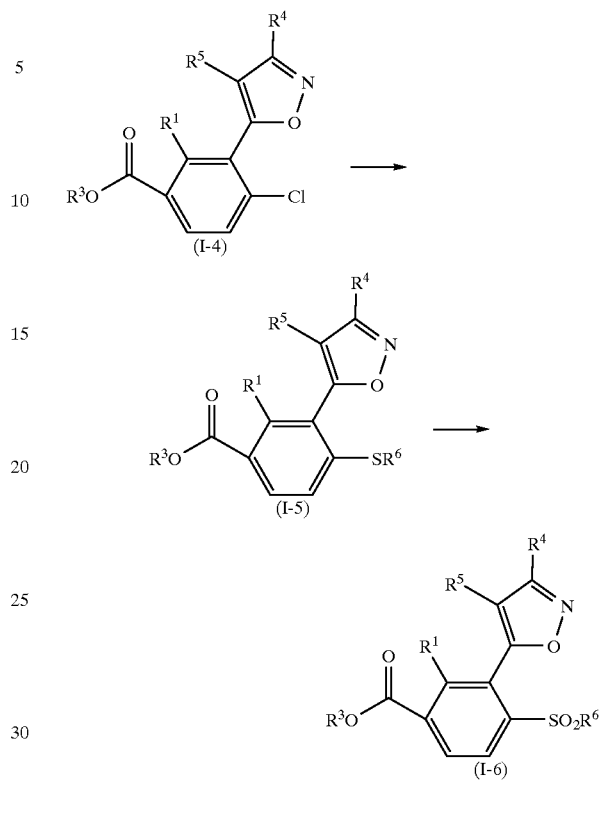

(wherein $R^1$, $R^2$, $R^3$, $R^4$, and $R^5$ have the same meanings as defined above and $r_1$ and $r_2$ each represent a lower alkyl group).

The isoxazole compound represented by the general formula [I-3] can be produced by causing 1–20 equivalent weights of a N,N-dialkylalkyl amide dialkyl acetal to react with the acyl compound [V] thereby forming a dialkyl amino methylidene compound [VI], then converting this compound [VI] into a corresponding hydroxyl imino compound [VIII] by the action of hydroxyl amine therewith, and then closing an open ring remaining in the compound.

The reaction for producing the dialkyl amino methylidene compound [VI] is carried out in a N,N-dialkylalkyl amide dialkyl acetal such as N,N-dimethyl formamide dimethyl acetal, N,N-diethyl formamide diethyl acetal, or N,N-dimethyl acetamide dimethyl acetal or in an inert solvent such as DMF or xylene at a temperature in the range between room temperature and the boiling point of the solvent to be used.

The reaction for producing the hydroxyl imino compound [VIII] is effected by 1.01–2.0 equivalent weights of hydroxy amine with the compound [VI]. The hydroxy amine is used in the form of a hydrochloride or a sulfate.

The ring-closing reaction for producing the compound [I-3] from the hydroxyl imino compound [VIII] is effected by refluxing the compound [VIII] in a solvent such as benzene, toluene, or xylene in the presence of an acid catalyst such as concentrated sulfuric acid, p-toluene sulfonic acid, or hydrochloric acid.

The compound represented by the formula [I-6] can be obtained by causing a mercaptan represented by $R^6SH$ to react on a 2,4-dichloro compound in the presence of a base thereby obtaining a 4-alkylthio compound [I-5] and then oxidizing the compound [I-5].

As concrete examples of the mercaptan to be used for the reaction, methyl mercaptan, ethyl mercaptan, n-propyl mercaptan, and isopropyl mercaptan may be cited. As concrete examples of the base for the reaction, alcoholates such as sodium methylate and sodium ethylate, alkali metal hydroxides such as sodium hydroxide and potassium hydroxide, carbonates such as sodium carbonate and potassium carbonate, and organic bases such as triethyl amine, diisopropyl ethyl amine, and pyridine may be cited.

Alternatively, a mercaptan salt such as sodium salt of methyl mercaptan may be prepared from mercaptan and a base and this mercaptan salt may be used for the reaction with the compound represented by the formula [I-4].

As concrete examples of the oxidizing agent which can be used for the oxidation reaction at the final step, hydrogen peroxide, hypochlorites such as sodium hypochloride and calcium hypochloride and organic peroxides such as peracetic acid, perbenzoic acid, and m-chloro-perbenzoic acid may be cited.

(5) Method of production 5

Besides the methods described above, the compound of this invention can be produced by the method of production disclosed in the form of a general formula in the official gazette of WO96/26206.

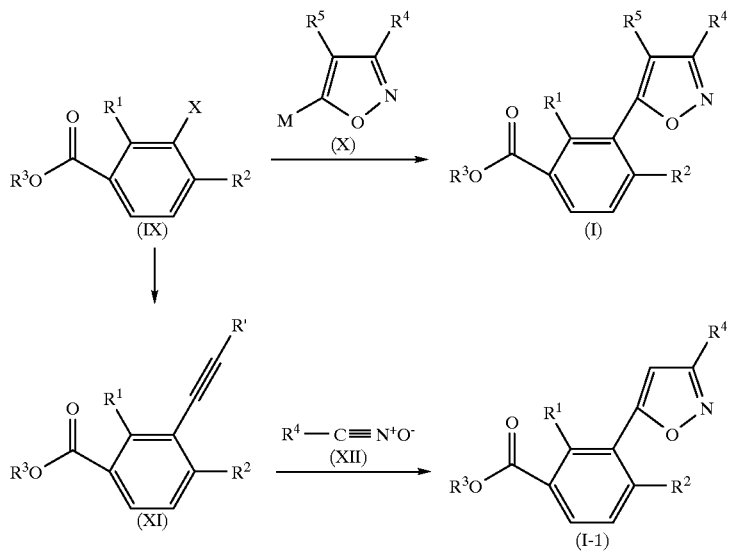

(wherein $R^1$, $R^2$, $R^3$, $R^4$, and $R^5$ have the same meanings as defined above, R' represents a hydrogen atom or a trimethyl silyl group, X represents a halogen atom or an eliminating group such as trifluoromethyl group, and M represents $Sn(C_{1-6})_3$, $B(OH)_2$, or ZnCl).

Specifically, the compound of this invention represented by the formula [I] can be obtained by causing an organic metal compound represented by the formula [X] to react with a compound represented by the formula [IX] in the presence of a palladium catalyst. The compound represented by the formula [I-1] can be otherwise obtained, for example, by causing an alkine such as trimethyl silyl acetylene to react with a compound represented by the formula [IX] in the presence of a catalyst such as cuprous iodide thereby obtaining a compound represented by the formula [XI] (R'=TMS), converting this compound by hydrolysis into a compound having a hydrogen atom for R', and causing this compound to react with a compound represented by the formula [XII] and obtained by the reaction of an oxidizing agent such as a hypochloride with an alkoxide compound.

The compounds and various intermediates of this invention can be finished by the standard aftertreatment which is performed after the relevant reactions. The structures of the compounds and various intermediates of this invention are determined by IR, NMR, MS, etc.

BEST MODE FOR EMBODYING THE INVENTION

Now, the compounds of this invention will be described more specifically below with reference to working examples.

(EXAMPLE 1)

Production of 2,4-dichloro-3-(3-methyl-1,2-ispooxazol-5-yl) benzoic acid

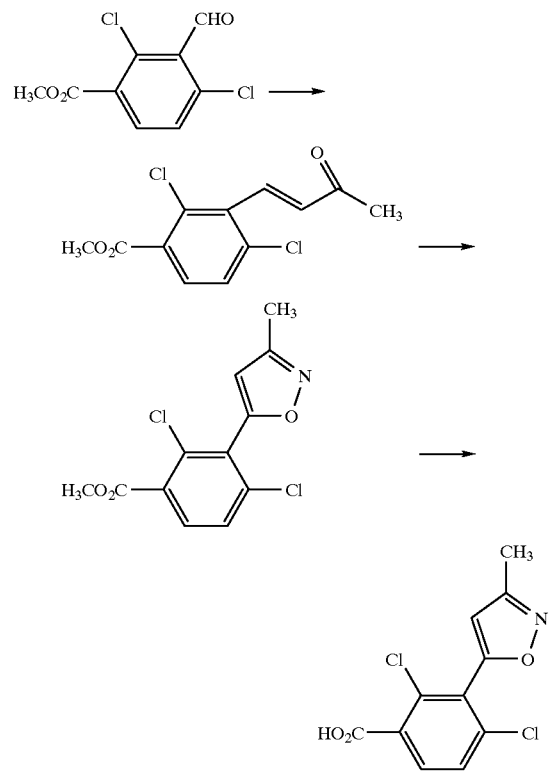

A solution of 24.7 g (0.1 mol) of methyl 3-formyl-2,4-dichlorobenzoate in a solvent consisting of 120 ml of acetone and 12 ml of water was kept cooled below 20° C. with ice water and 35 ml of an aqueous 1-N caustic soda solution was added dropwise thereto over a period of 30 minutes. After the dropwise addition was completed, the resultant mixture was further stirred overnight at room temperature. The reaction mixture was poured into ice water, acidified with concentrated hydrochloric acid, and extracted from ethyl acetate. The ethyl acetate layer was washed with saturated saline solution, dried over magnesium sulfate, and concentrated under a reduced pressure. The residue was dissolved in benzene. The resultant solution and a catalytic amount of p-toluene sulfonic acid added thereto were refluxed for four hours with the removal of the formed water continued meanwhile. The reaction solution was left cooling, washed with saturated saline solution, dried over magnesium sulfate, and distilled under a reduced pressure to expel the solvent. When the residue was refined by silica gel column chromatography, 15.4 g of methyl 2,4-dichloro-3-(3-oxo-1-butenyl) benzoate was obtained. Yield 54.8%.

In a mixed solvent consisting of 80 ml of ethanol and 80 ml of pyridine, 15.4 g (0.056 mol) of methyl 3-(3-oxo-1-butenyl)-2,4-dichlorobenzoate and 15 g (0.216 mol) of hydroxy amine hydrochloride were dissolved. The solution was refluxed for two hours. The reaction mixture was poured into ice water and extracted from ethyl acetate. The ethyl acetate layer was washed with 1 N hydrochloric acid and then with saturated saline solution, dried over magnesium sulfate, and distilled under a reduced pressure to expel the solvent and obtain 15.9 g of methyl 2,4-dichloro-3-(3-hydroxyimino-1-butenyl) benzoate. Yield 98.2%.

A solution of 15.9 g (0.052 mol) of 2,4-dichloro-3-(3-hydroxyimino-1-butenyl) benzoate in 250 ml of tetrahydrofuran, a solution of 16.8 g (0.2 mol) of sodium hydrogen bicarbonate in 160 ml of water added thereto, and an aqueous solution obtained by dissolving 30.1 g (0.18 mol) of potassium iodide and 14 g (0.055 mol) of iodine in 120 ml further added thereto were refluxed together as shielded from light for four hours. The reaction mixture was poured into ice water, combined with sodium hydrogen sulfite, and extracted from ethyl acetate. The organic layer was washed with saturated saline solution, dried over magnesium sulfate, and distilled under a reduced pressure to expel the solvent. When the residue was refined by silica gel column chromatography, 8.8 g of methyl 2,4-dichloro-3-(3-methylisoxazol-5-yl) benzoate was obtained. Yield 54.5% and mp. 84–89° C.

A solution of 2.0 g (0.0069 mol) of methyl 2,4-dichloro-3-(3-methylisoxazol-5-yl) benzoate in 21 ml of ethyl alcohol and 21 ml of an aqueous 1-N caustic soda solution added thereto were stirred together overnight at room temperature. The reaction mixture was poured into ice water and acidified with concentrated hydrochloric acid. The crystals consequently educed were separated by filtration, washed with water, and dried to obtain 1.86 g of 2,4-dichloro-3-(3-methylisooxazol-5-yl) benzoic acid. Yield 97.9% and mp 154–156° C.

(EXAMPLE 2)

Production of 2-chloro-4-methane sulfonyl-3-(3-methylisoxazol-5-yl) benzoic acid

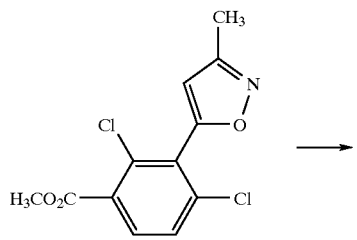

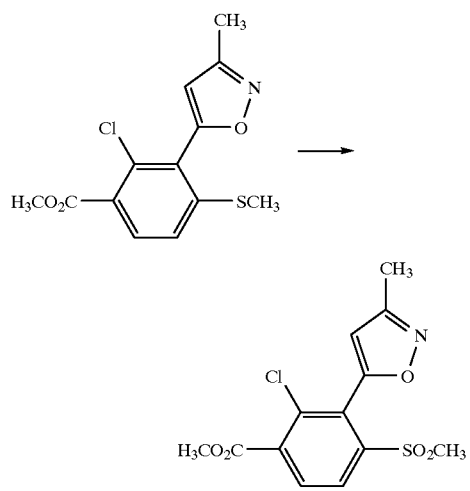

A solution of 8.8 g (0.030 mol) of methyl-2,4-dichloro-3-(3-methylisoxazol-5-yl) benzoate and 4.3 g (0.030 mol) of potassium carbonate in 20 ml of dimethyl formamide and a solution of 1.9 g (0.038 mol) of methane thiol in 10 ml of dimethyl formamide added thereto were stirred together overnight at room temperature. The reaction mixture was poured into ice water, extracted from ethyl acetate, washed with saturated saline solution, dried over magnesium sulfate, and distilled under a reduced pressure to expel the solvent. When the residue was refined by silica gel column chromatography, 7.49 g of methyl 2-chloro-3-(3-methylisoxazol-5-yl)-4-methylthiobenzoate was obtained. Yield 82%.

A solution of 7.49 g (0.025 mol) of methyl 2-chloro-3-(3-methylisoxazol-5-yl)-4-methylthiobenzoate in 30 ml of chloroform and 13 g (0.074 mol) of m-chloroperbenzoic acid added thereto were stirred together at room temperature for three hours. The reaction mixture was filtered. The filtrate was washed with an aqueous 1-N caustic soda solution and then with saturated saline solution, dried over magnesium sulfate, and distilled under a reduced pressure to expel the solvent. The residue was refined by silica gel column chromatography to obtain 8.19 g of methyl 3-(3-methylisoxazol-5-yl)-2-chloro-4-methane sulfonyl benzoate. Yield 99% and mp. 138–139° C.

A solution of 8.19 g (0.024 mol) of methyl 2-chloro-4-methane sulfonyl-3-(3-methylisoxazol-5-yl) benzoate in 75 ml of ethyl alcohol and 75 ml of an aqueous 1-N caustic soda solution added thereto were stirred together overnight at room temperature. The reaction mixture was poured into ice water and acidified with concentrated hydrochloric acid. The crystals educed consequently were separated by filtration, washed with water, and dried to obtain 7.49 g of white crystals as aimed at. Yield 96% and mp. 225–228° C.

(EXAMPLE 3)

Production of methyl 2,4-dichloro-3-(4-methylisoxazol-5-yl) benzoate

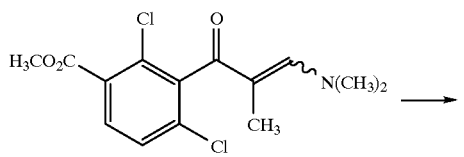

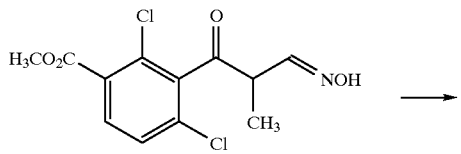

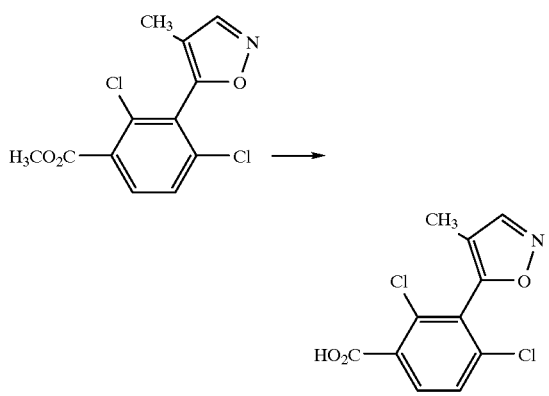

A solution of 7.57 g of methyl 2,4-dichloro-3-(2-dimethyl aminomethylidene-1-oxopropyl) benzoate in 30 ml of dioxane and 16 ml of water and 1.70 g of hydroxyl amine hydrochloride added thereto were stirred together at room temperature for 17 hours. The reaction mixture was distilled under a reduced pressure to expel the solvent. The residue was dissolved in ethyl acetate, washed with saturated saline solution, and dried over magnesium sulfate. The solution was distilled under a reduced pressure to expel the solvent. The crude oxime compound consequently obtained was dissolved in 30 ml of toluene. The resultant solution and 0.5 g of p-toluene sulfonic acid added thereto were refluxed together for 14.5 hours. The reaction solution was cooled, washed with water, washed with saturated saline solution, and dried over magnesium sulfate. The solution was distilled under a reduced pressure to expel the solvent. When the residue was refined by silica gel column chromatography, 0.83 g of methyl 2,4-dichloro-3-(4-methylisoxazol-5-yl) benzoate was obtained.

(EXAMPLE 4)

Production of 2,4-dichloro-3-(4-methylisoxazol-5-yl) benzoic acid

A solution of 0.83 g of methyl 2-4-dichloro-3-(4-methylisooxazol-5-yl) benzoate in 20 ml of dioxane and 5 ml of concentrated hydrochloric acid added thereto were refluxed together for 15.5 hours. The solution was cooled, distilled to expel dioxane, and extracted from ethyl acetate. The organic layer was washed with saturated saline solution and dried over magnesium sulfate. The solution was distilled under a reduced pressure to expel the solvent. When the residue was refined by silica gel column chromatography, 0.48 g of 2,4-dichloro-3-(4-methylisoxazol-5-yl) benzoic acid aimed at was obtained in the form of crystals. mp. 248–252° C.

Examples of the compound of this invention obtained as described above are shown in Table 1.

(Referential Example) Production of intermediates for synthesis

Referential Example 1

Production of methyl 2,4-dichloro-3-formyl benzoate

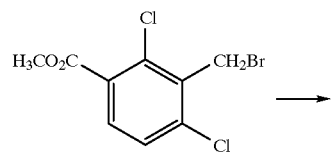

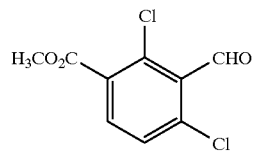

One hundred (100) ml of methanol and 26.61 g of a methanol 28% sodium methylate solution added thereto were kept cooled below 25° C. with ice and 12.29 g of 2-nitropropane was added dropwise thereto. Then, the resultant mixture and 41.16 g of methyl 3-bromomethyl-2,4-dichlorobenzoate added thereto were refluxed together for 30 minutes. The reaction solution was cooled and distilled under a reduced pressure. The residue was dissolved in 1000 ml of ethyl acetate, kept cooled with ice, and washed with an aqueous 1% sodium hydroxide solution. The organic layer was washed with water, then with saturated saline solution, and dried over magnesium sulfate. The solution was distilled under a reduced pressure to expel the solvent and obtain crystals. The crystals were washed with benzene and then with n-hexane to obtain 22.00 g of methyl 2,4-dichloro-3-formyl benzoate aimed at in the form of crystals. mp. 103–104° C.

Referential Example 2

Production of 2,4-dichloro-3-formyl benzoic acid

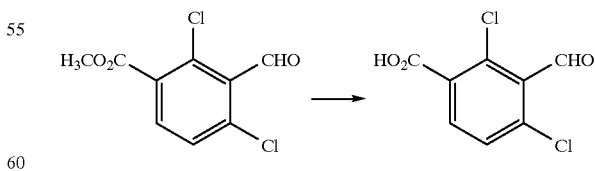

A solution of 1.04 g of methyl 2,4-dichloro-3-formyl benzoate in 5 ml of ethanol and 10 ml of an aqueous 1-N sodium hydroxide solution added thereto were stirred together at room temperature for 17 hours. The reaction solution was poured into 40 ml of ice water and acidified with concentrated hydrochloric acid. The crystals consequently educed were separated by filtration and dried to obtain 0.75 g of 2,4-dichloro-3-formyl benzoic acid aimed at in the form of crystals. mp. 188–190° C.

Referential Example 3

Production of 2,6-dichloro-3-methoxycarbonyl benzoic acid

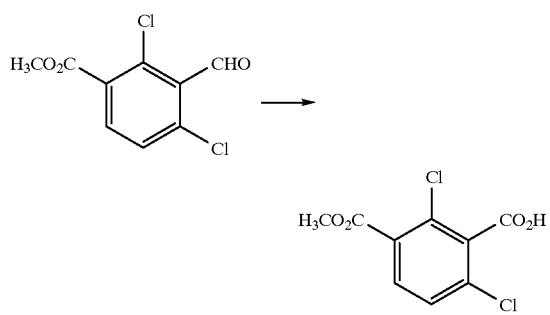

A solution of 24.2 g of methyl 2,4-dichloro-3-formyl benzoate in 350 ml of acetone and 55 ml of Jones reagent prepared as taught in J. Chem. Soc., 1953 (2548) added dropwise thereto were left reacting at a temperature in the range of 10–15° C. They were stirred at a temperature below 10° C. for 1.5 hours. The reaction solution and 50 ml of isopropyl alcohol and 20 g of sodium bicarbonate added thereto were stirred together for 30 minutes. The resultant mixture was filtered to separate an insoluble portion. The filtrate was concentrated, mixed with 300 ml of water, and extracted from 300 ml of ethyl acetate. The organic layer was washed with saturated saline solution and then dried over magnesium sulfate. The solution was distilled under a reduced pressure to expel and solvent and obtain 25.0 g of 2,6-dichloro-3-methoxycarbonyl benzoic acid as aimed at in the form of crystals.

Referential Example 4

Production of methyl 2,4-dichloro-3-(1-oxoethyl) benzoate

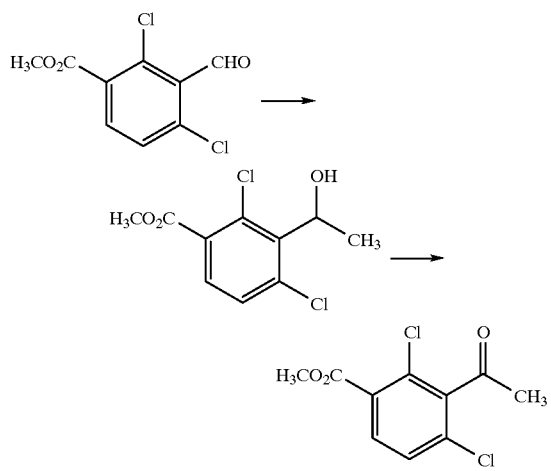

A solution of 2.47 g of methyl 2,4-dichloro-3-formyl benzoate in 20 ml of dry THF was kept cooled to −70° C. and 4 ml of a diethyl ether solution of methyl magnesium bromide (3.0 mol/Λ was slowly added dropwise thereto. After the dropwise addition was completed, the resultant mixture was removed from the cooling bath, left spontaneously warming, and stirred for one hour. The reaction mixture was poured into ice water, acidified with dilute hydrochloric acid, and extracted from diethyl ether. The organic layer was washed with saturated saline solution and dried over magnesium sulfate. The solution was distilled under a reduced pressure to expel the solvent and obtain 2.42 g of methyl 2,4-dichloro-3-(1-hydroxyethyl) benzoate aimed at in the form of an oily substance. Then, a solution of 2.42 g of methyl 2,4-dichloro-3-(1-hydroxyethyl) benzoate in 10 ml of benzene and 4 g of manganese dioxide added thereto were refluxed together for one hour. The resultant solution and 3 g of manganese dioxide added thereto were refluxed together for one hour. The reaction solution was cooled to room temperature and filtered to separate an insoluble portion. The filtrate was distilled under a reduced pressure to expel the solvent and obtain 1.75 g of methyl 2,4-dichloro-3-(1-oxoethyl)benzoate aimed at. $nD^{23}$ 1.5495.

Referential Example 5

Production of methyl 2,4-dichloro-3-(2-oxopropyl) benzoate

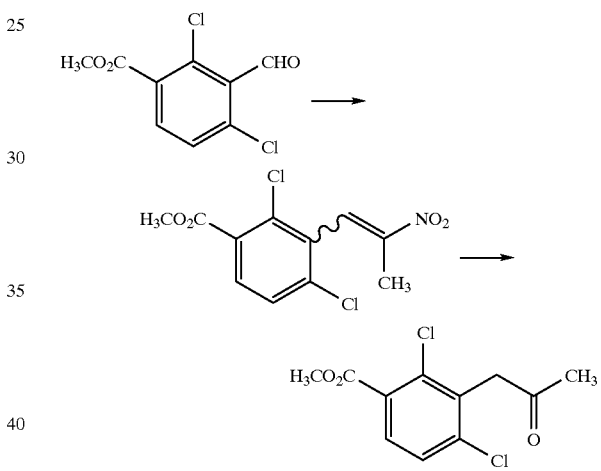

A solution of 25.72 g of methyl 2,4-dichloro-3-formyl benzoate in 100 ml of toluene and 39.0 g of nitroethane and 1.5 g of n-butyl amine added thereto were refluxed together for 21 hours. The reaction solution was poured into ice, extracted from ethyl acetate, washed with 1-N hydrochloric acid, then with saturated saline solution, and dried over magnesium sulfate. The solution was distilled under a reduced pressure to expel the solvent and obtain 34.9 g of methyl 2,4-dichloro-3-(2-nitro-1-propenyl) benzoate. A solution of 30.1 g of the benzoate so obtained in a mixed solvent consisting of 120 ml of toluene and 360 ml of water was mixed with 20.8 g of iron powder and 0.4 g of ferric chloride. To the mixture, 104 g of concentrated hydrochloric acid was added dropwise at 80° C. After the dropwise addition was completed, the resultant mixture was further left reacting as refluxed for one hour. The reaction solution was cooled, mixed with ethyl acetate, and filtered to separate an insoluble portion. The organic layer was washed with water, then with saturated saline solution, and dried over magnesium sulfate. The solution was distilled under a reduced pressure to expel the solvent. When the residue was refined by silica gel chromatography, 19.53 g of methyl 2,4-dichloro-3-(2-oxopropyl) benzoate was obtained. $nD^{22}$ 1.5537.

Referential Example 6

Production of 2,6-dichloro-3-methoxycarbonyl benzoyl acetone

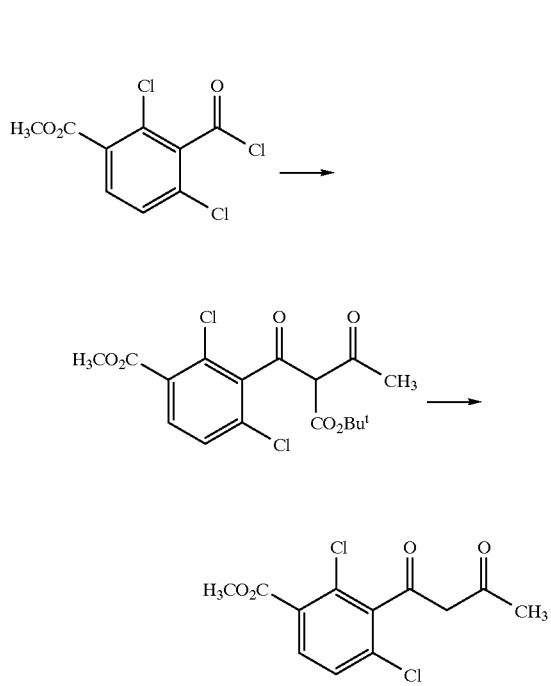

A suspension of 1.65 g of magnesium ethylate in 30 ml of toluene was kept at 60–70° C. and 2.28 g of acetoacetic tert-butyl ester was added dropwise thereto. After the dropwise addition was completed, the resultant mixture was refluxed for two hours. Then, the reaction solution was cooled to room temperature and 3.85 g of 2,6-dichloro-3-methoxycarbonyl benzoic acid chloride was added dropwise thereto. The reaction mixture was stirred at room temperature for two hours and at 50–100° C. for three hours, then cooled to room temperature, treated with dilute hydrochloric acid, and extracted from ethyl acetate. Then, the organic layer was alkali extracted from an aqueous 5% sodium carbonate solution. The water layer was mixed with chloroform, educed with dilute hydrochloric acid, and extracted again. The organic layer was washed with saturated saline solution and dried over magnesium sulfate. The solution was distilled under a reduced pressure to expel the solvent and obtain 2.80 g of 2-(2,6-dichloro-3-methoxycarbonyl benzoyl) acetoacetic tert-butyl ester. A solution of this ester in 45 ml of toluene and 0.2 g of p-toluene sulfonic acid hydrate added thereto were refluxed together for six hours. The reaction solution was cooled, mixed with 200 ml of ethyl acetate, washed twice with 200 ml of water, further washed with saturated saline solution, and dried over magnesium sulfate. The solution was distilled under a reduced pressure to expel the solvent and obtain 2.10 g of 2,6-dichloro-3-methoxycarbonyl benzoyl acetone. $nD^{22}$ 1.5759.

Reference 7

Production of 4-[2-chloro-3-(3-methylisoxazol-5-yl)-4-methyl sulfonyl benzoyl]-1-ethyl-5-hydroxy pyrazole

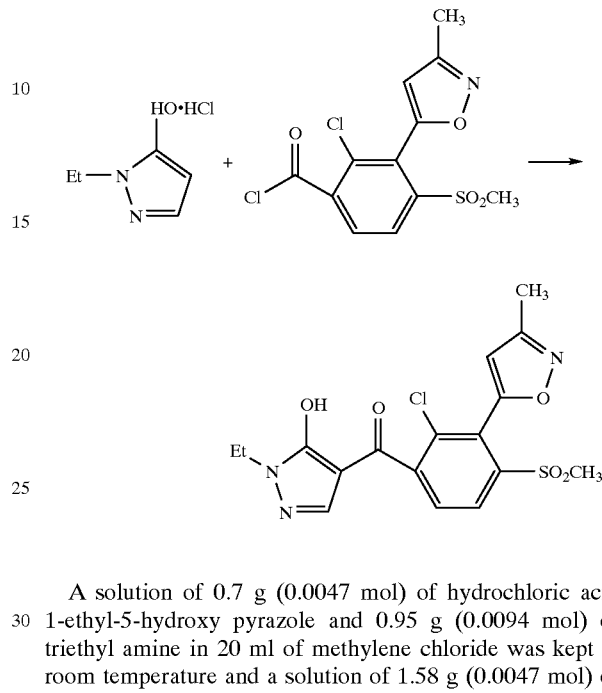

A solution of 0.7 g (0.0047 mol) of hydrochloric acid 1-ethyl-5-hydroxy pyrazole and 0.95 g (0.0094 mol) of triethyl amine in 20 ml of methylene chloride was kept at room temperature and a solution of 1.58 g (0.0047 mol) of 2-chloro-4-methane sulfonyl-3-(3-methylisoxazol-5-yl) benzoyl chloride in 5 ml of methylene chloride was added dropwise thereto and they were stirred together at room temperature for one hour. The reaction mixture was washed with 1-N hydrochloric acid, then with saturated saline solution, dried over magnesium sulfate, and distilled under a reduced pressure to expel the solvent. The residue was dissolved in 20 ml of acetonitrile, mixed with 0.47 g (0.0047 mol) of triethyl amine and 0.1 g (0.0011 mol) of acetone cyan hydrin, and stirred at room temperature overnight. The solution was distilled under a reduced pressure to expel the solvent. The residue was dissolved in ethyl acetate, washed with 1-N hydrochloric acid, then with saturated saline solution, dried over magnesium sulfate, and then distilled under a reduced pressure to expel the solvent. When the residue was refined by silica gel column chromatography, 0.73 g of the captioned compound was obtained. mp. 230–233° C.

Referential Example 8

Production of 4-[2-chloro-3-(3-methylisoxazol-5-yl)-4-methane sulfonyl benzoyl]-5-hydroxy-1-methyl pyrazole

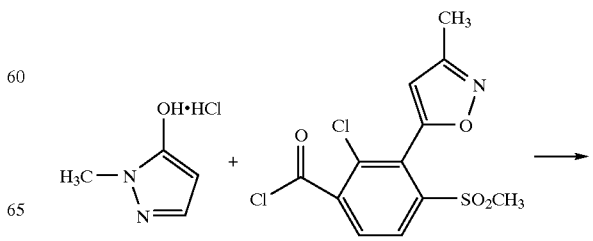

-continued

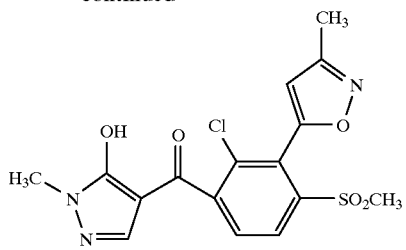

A solution of 6.31 g of hydrochloric acid 5-hydroxy-1-methyl pyrazole and 14.15 g of 2-chloro-3-(3-methylisoxazol-5-yl)-4-methane sulfonyl benzoyl chloride in 65 ml of chloroform and 9.54 g of triethyl amine was added thereto as kept cooled with ice and they were stirred together overnight at room temperature. The reaction mixture was washed with dilute hydrochloric acid, with saturated aqueous sodium bicarbonate solution, and then with saturated saline solution, dried over magnesium sulfate, and distilled under a reduced pressure to expel the solvent and obtain 11.65 g of a residue. A solution of this residue in 70 ml of acetonitrile and 4.00 g of triethyl amine and 0.85 g of acetone cyan hydrin added thereto were stirred together at room temperature for one hour. The solution was distilled under a reduced pressure to expel the solvent. The residue was dissolved in ethyl acetate, washed with 1-N hydrochloric acid, then with saturated saline solution, dried over magnesium sulfate, and distilled under a reduced pressure to expel the solvent. When the residue was refined by silica gel column chromatography, 5.00 g of the captioned compound was obtained. mp. 106–108° C. (crystallized from toluene). mp. 239–241° C. (crystallized from methanol).

Referential Example 9

Production of 4-[2,4-dichloro-3-(3-methylisoxazol-5-yl)benzoyl]-1-ethyl-5-hydroxy pyrazole

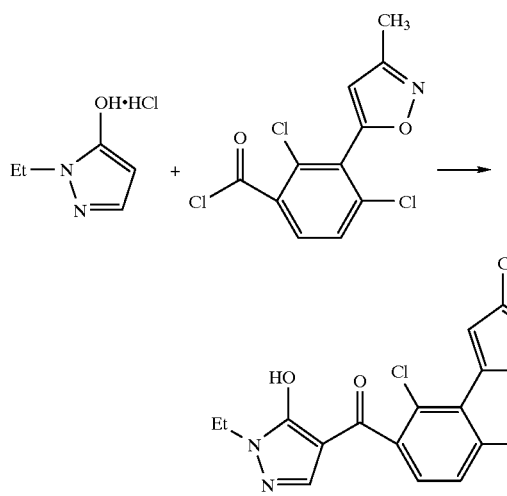

A solution of 4.46 g of hydrochloric acid 1-ethyl-5-hydroxy pyrazole and 8.24 g of 2,4-dichloro-3-(3-methylisoxazol-5-yl) benzoyl chloride in 40 ml of chloroform and 6.36 g of triethyl amine was added dropwise thereto as kept with water. Then, they were stirred together at room temperature for 25 minutes. The reaction mixture and 3.64 g of triethyl amine and 0.51 g of acetone cyan hydrin added thereto were stirred together at room temperature overnight. The reaction mixture was mixed with water and alkalinized with an aqueous 10% sodium hydroxide solution. The aqueous sodium salt solution consequently obtained was adjusted to pH 4 by the addition of dilute hydrochloric acid and extracted from ethyl acetate. The organic layer was washed with water and saturated saline solution, dried over magnesium sulfate, and distilled to expel the solvent. The residue was mixed with methanol. The crystals consequently educed were separated by filtration to obtain 4.82 g of the captioned compound. mp. 174–178° C.

TABLE 1

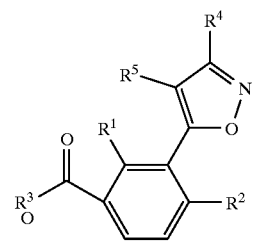

| Compound No. | $R^3$ | $R^1$ | $R^2$ | $R^4$ | $R^5$ | Physical property °C. |
|---|---|---|---|---|---|---|
| I-1 | H | Cl | Cl | H | H | [144–146] |
| I-2 | $CH_3$ | Cl | Cl | H | H | |
| I-3 | H | Cl | $SO_2CH_3$ | H | H | [215–220] |
| I-4 | $CH_3$ | Cl | $SO_2CH_3$ | H | H | [131–134] |
| I-5 | H | Cl | Cl | $CH_3$ | H | [154–156] |
| I-6 | $CH_3$ | Cl | Cl | $CH_3$ | H | [84–89] |
| I-7 | H | Cl | $SO_2CH_3$ | $CH_3$ | H | [225–228] |
| I-8 | $CH_3$ | Cl | $SO_2CH_3$ | $CH_3$ | H | [138–139] |
| I-9 | H | Cl | Cl | H | $CH_3$ | [248–252] |
| I-10 | $CH_3$ | Cl | Cl | H | $CH_3$ | *1 |
| I-11 | H | Cl | $SO_2CH_3$ | H | $CH_3$ | |
| I-12 | $CH_3$ | Cl | $SO_2CH_3$ | H | $CH_3$ | |
| I-13 | H | Cl | Cl | $C_2H_5$ | H | [156–159] |
| I-14 | Et | Cl | Cl | $C_2H_5$ | H | |
| I-15 | H | Cl | $SO_2CH_3$ | $C_2H_5$ | H | [148–150] |
| I-16 | $CH_3$ | Cl | $SO_2CH_3$ | $C_2H_5$ | H | |
| I-17 | H | Cl | Cl | H | $C_2H_5$ | |
| I-18 | $CH_3$ | Cl | Cl | H | $C_2H_5$ | |
| I-19 | H | Cl | $SO_2CH_3$ | H | $C_2H_5$ | |
| I-20 | $CH_3$ | Cl | $SO_2CH_3$ | H | $C_2H_5$ | |
| I-21 | H | Cl | Cl | i-Pr | H | |
| I-22 | $CH_3$ | Cl | Cl | i-Pr | H | |
| I-23 | H | Cl | $SO_2CH_3$ | i-Pr | H | |
| I-24 | $CH_3$ | Cl | $SO_2CH_3$ | i-Pr | H | |
| I-25 | H | Cl | Cl | $CH_3$ | $CH_3$ | *2 |
| I-26 | $CH_3$ | Cl | Cl | $CH_3$ | $CH_3$ | |
| I-27 | H | Cl | $SO_2CH_3$ | $CH_3$ | $CH_3$ | [181–184] |
| I-28 | $CH_3$ | Cl | $SO_2CH_3$ | $CH_3$ | $CH_3$ | |
| I-29 | H | $CH_3$ | Cl | H | H | |
| I-30 | $CH_3$ | $CH_3$ | Cl | H | H | |
| I-31 | H | $CH_3$ | $SO_2CH_3$ | H | H | |
| I-32 | $CH_3$ | $CH_3$ | $SO_2CH_3$ | H | H | |
| I-33 | H | $CH_3$ | Cl | $CH_3$ | H | |
| I-34 | Et | $CH_3$ | Cl | $CH_3$ | H | |
| I-35 | H | $CH_3$ | $SO_2CH_3$ | $CH_3$ | H | [242–244] |
| I-36 | $CH_3$ | $CH_3$ | $SO_2CH_3$ | $CH_3$ | H | |
| I-37 | H | $CH_3$ | Cl | H | $CH_3$ | |
| I-38 | $CH_3$ | $CH_3$ | Cl | H | $CH_3$ | |
| I-39 | H | $CH_3$ | $SO_2CH_3$ | H | $CH_3$ | |
| I-40 | $CH_3$ | $CH_3$ | $SO_2CH_3$ | H | $CH_3$ | |
| I-41 | H | $CH_3$ | Cl | $C_2H_5$ | H | |
| I-42 | Et | $CH_3$ | Cl | $C_2H_5$ | H | |
| I-43 | H | $CH_3$ | $SO_2CH_3$ | $C_2H_5$ | H | |
| I-44 | $CH_3$ | $CH_3$ | $SO_2CH_3$ | $C_2H_5$ | H | |
| I-45 | H | $CH_3$ | Cl | $CH_3$ | $CH_3$ | |
| I-46 | $CH_3$ | $CH_3$ | Cl | $CH_3$ | $CH_3$ | |
| I-47 | H | $CH_3$ | $SO_2CH_3$ | $CH_3$ | $CH_3$ | |
| I-48 | $CH_3$ | $CH_3$ | $SO_2CH_3$ | $CH_3$ | $CH_3$ | |
| I-49 | H | $OCH_3$ | Cl | H | H | |

TABLE 1-continued

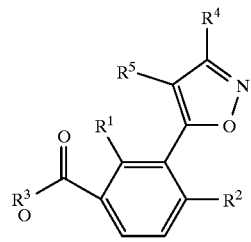

| Compound No. | R³ | R¹ | R² | R⁴ | R⁵ | Physical property °C. |
|---|---|---|---|---|---|---|
| I-50 | CH₃ | OCH₃ | Cl | H | H | |
| I-51 | H | OCH₃ | SO₂CH₃ | H | H | |
| I-52 | CH₃ | OCH₃ | SO₂CH₃ | H | H | |
| I-53 | H | OCH₃ | Cl | CH₃ | H | *3 |
| I-54 | CH₃ | OCH₃ | Cl | CH₃ | H | |
| I-55 | H | OCH₃ | SO₂CH₃ | CH₃ | H | [185–188] |
| I-56 | CH₃ | OCH₃ | SO₂CH₃ | CH₃ | H | |
| I-57 | H | OCH₃ | Cl | H | CH₃ | |
| I-58 | CH₃ | OCH₃ | Cl | H | CH₃ | |
| I-59 | H | OCH₃ | SO₂CH₃ | H | CH₃ | |
| I-60 | CH₃ | OCH₃ | SO₂CH₃ | H | CH₃ | |
| I-61 | H | OCH₃ | Cl | C₂H₅ | H | |
| I-62 | CH₃ | OCH₃ | Cl | C₂H₅ | H | |
| I-63 | H | OCH₃ | SO₂CH₃ | C₂H₅ | H | |
| I-64 | CH₃ | OCH₃ | SO₂CH₃ | C₂H₅ | H | |
| I-65 | H | OCH₃ | Cl | CH₃ | CH₃ | |
| I-66 | CH₃ | OCH₃ | Cl | CH₃ | CH₃ | |
| I-67 | H | OCH₃ | SO₂CH₃ | CH₃ | CH₃ | |
| I-68 | CH₃ | OCH₃ | SO₂CH₃ | CH₃ | CH₃ | |
| I-69 | H | SO₂CH₃ | Cl | H | H | |
| I-70 | CH₃ | SO₂CH₃ | Cl | H | H | |
| I-71 | H | SO₂CH₃ | Cl | CH₃ | H | [221–222] |
| I-72 | CH₃ | SO₂CH₃ | Cl | CH₃ | H | [149.5–150.5] |
| I-73 | H | SO₂CH₃ | Cl | H | CH₃ | |
| I-74 | CH₃ | SO₂CH₃ | Cl | H | CH₃ | |
| I-75 | H | SO₂Et | Cl | C₂H₅ | H | |
| I-76 | CH₃ | SO₂Et | Cl | C₂H₅ | H | |
| I-77 | H | SO₂CH₃ | Cl | CH₃ | CH₃ | |
| I-78 | CH₃ | SO₂CH₃ | Cl | CH₃ | CH₃ | |
| I-79 | H | Cl | SCH₃ | H | H | |
| I-80 | CH₃ | Cl | SCH₃ | H | H | |
| I-81 | H | Cl | SCH₃ | CH₃ | H | [175–177] |
| I-82 | CH₃ | Cl | SCH₃ | CH₃ | H | |
| I-83 | H | Cl | SCH₃ | CH₃ | CH₃ | |
| I-84 | CH₃ | Cl | SCH₃ | CH₃ | CH₃ | |
| I-85 | H | Cl | SOCH₃ | H | H | |
| I-86 | CH₃ | Cl | SOCH₃ | H | H | |
| I-87 | H | Cl | SOCH₃ | CH₃ | H | [221–222] |
| I-88 | CH₃ | Cl | SOCH₃ | CH₃ | H | |
| I-89 | H | Cl | SOCH₃ | CH₃ | CH₃ | |
| I-90 | CH₃ | Cl | SOCH₃ | CH₃ | CH₃ | |
| I-100 | H | CH₃ | SCH₃ | H | H | |
| I-101 | CH₃ | CH₃ | SCH₃ | H | H | |
| I-102 | H | CH₃ | SCH₃ | H | CH₃ | |
| I-103 | CH₃ | CH₃ | SCH₃ | H | CH₃ | |
| I-104 | H | CH₃ | SCH₃ | CH₃ | CH₃ | |
| I-105 | CH₃ | CH₃ | SCH₃ | CH₃ | CH₃ | |
| I-106 | H | CH₃ | SOCH₃ | H | H | |
| I-107 | CH₃ | CH₃ | SOCH₃ | H | H | |
| I-108 | H | Br | Cl | H | CH₃ | |
| I-109 | CH₃ | Br | Cl | H | CH₃ | |
| I-110 | H | Br | SO₂CH₃ | H | CH₃ | |
| I-111 | CH₃ | Br | SO₂CH₃ | H | CH₃ | |
| I-112 | H | F | Cl | H | CH₃ | |
| I-113 | CH₃ | F | Cl | H | CH₃ | |
| I-114 | H | F | SO₂CH₃ | H | CH₃ | |
| I-115 | CH₃ | F | SO₂CH₃ | H | CH₃ | |
| I-116 | H | Cl | SO₂Et | H | CH₃ | |
| I-117 | CH₃ | Cl | SO₂Et | H | CH₃ | |
| I-118 | H | CF₃ | Cl | H | CH₃ | |
| I-119 | CH₃ | CF₃ | Cl | H | CH₃ | |
| I-120 | H | CF₃ | SO₂CH₃ | H | CH₃ | |
| I-121 | CH₃ | CF₃ | SO₂CH₃ | H | CH₃ | |
| I-122 | H | Cl | CF₃ | H | CH₃ | |
| I-123 | CH₃ | Cl | CF₃ | H | CH₃ | |
| I-124 | H | OCF₃ | Cl | H | CH₃ | |
| I-125 | CH₃ | OCF₃ | Cl | H | CH₃ | |
| I-126 | H | OCF₃ | SO₂CH₃ | H | CH₃ | |
| I-127 | CH₃ | OCF₃ | SO₂CH₃ | H | CH₃ | |
| I-128 | H | CH₃ | SOCH₃ | H | CH₃ | |
| I-129 | CH₃ | CH₃ | SOCH₃ | H | CH₃ | |
| I-130 | H | CH₃ | SOCH₃ | CH₃ | H | |
| I-131 | CH₃ | CH₃ | SOCH₃ | CH₃ | H | |
| I-132 | H | CH₃ | SOCH₃ | CH₃ | CH₃ | |
| I-133 | CH₃ | CH₃ | SOCH₃ | CH₃ | CH₃ | |
| I-134 | H | OCH₃ | SCH₃ | H | H | |
| I-135 | C₂H₅ | OCH₃ | SCH₃ | H | H | *4 |
| I-136 | H | OCH₃ | SCH₃ | H | CH₃ | |
| I-137 | CH₃ | OCH₃ | SCH₃ | H | CH₃ | |
| I-138 | H | OCH₃ | SOCH₃ | CH₃ | CH₃ | |
| I-139 | CH₃ | OCH₃ | SOCH₃ | CH₃ | CH₃ | |

(Note)
*1: ¹H-NMR (CDCl₃, δ ppm): 1.97 (3H, s), 3.96 (3H, s), 7.50 (1H, d), 7.89 (1H, d), 8.27 (1H, s)
*2: ¹H-NMR (CDCl₃, δ ppm): 1.98 (3H, s), 2.36 (3H, s), 7.52 (1H, d), 7.70 (1H, bs), 8.04 (1H, d)
*3: ¹H-NMR (CDCl₃, δ ppm): 2.45 (3H, s), 3.73 (3H, s), 6.41 (1H, s), 7.43 (1H, d), 8.16 (1H, d)
*4: n_D^{24} 1.5898

Industrial Applicability

This invention, as described above, concerns a novel 2,4-di-substituted-3-heteroyl benzoic acid and a method for the production thereof. The compound of this invention is an intermediate for the production of a herbicidally active pyrazole compound represented by the following formula [B]

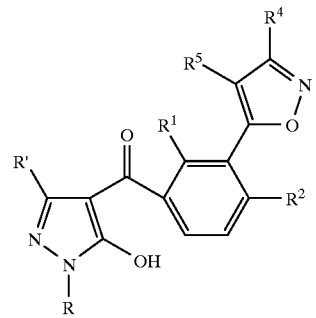

(wherein R, R', R¹, R², R⁴, and R⁵ have the same meanings as defined above).

The method of production according to this invention proves commercially advantageous (1) because it has no use for such raw materials as contain expensive metallic elements such as Sn and Si and allow no easy volume procurement, (2) because the reaction conditions are rela-

We claim:

1. A compound represented by the formula [I]

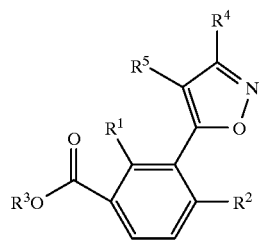

wherein $R^1$ represents a halogen atom, a $C_{1-4}$ alkyl group, a $C_{1-4}$ alkoxy group, a $C_{1-4}$ haloalkyl group, or a $C_{1-4}$ haloalkoxy group, $R^2$ represents a halogen atom, a $C_{1-4}$ alkyl group, a $C_{1-4}$ alkoxy group, a $C_{1-4}$ haloalkyl group, a $C_{1-4}$ haloalkoxy group, a $C_{1-4}$ alkylthio group, a $C_{1-4}$ alkylsulfinyl group, or a $C_{1-4}$ alkylsulfonyl group, $R^3$ represents a hydrogen atom or a $C_{1-6}$ alkyl group, and $R^4$ and $R^5$ independently represent a hydrogen atom or a $C_{1-6}$ alkyl group.

2. A method for the production of a compound represented by the formula [I-1]

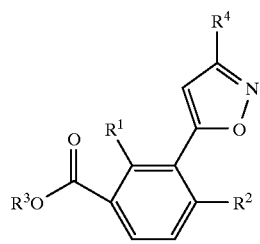

wherein $R^1$, $R^2$, $R^3$, and $R^4$ have the same meanings as defined above, comprising the steps of causing hydroxy amine or a hydroxy amine salt to react on a compound represented by the formula [II]

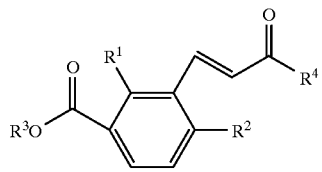

wherein $R^1$, $R^2$, $R^3$, and $R^4$ have the same meanings as defined above thereby forming a compound represented by the formula [III]

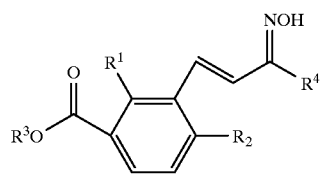

wherein $R^1$, $R^2$, $R^3$, and $R^4$ have the same meanings as defined above and then closing the open ring in said compound.

3. A method for the production of a compound represented by the formula [I]

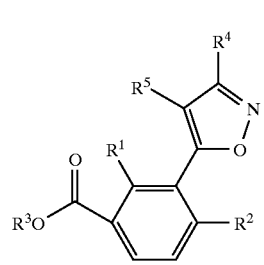

wherein $R^1$, $R^2$, $R^3$, $R^4$, and $R^5$ have the same meanings as defined above, comprising a hydroxy amine or a hydroxy amine salt to react with a compound represented by the formula [IV]

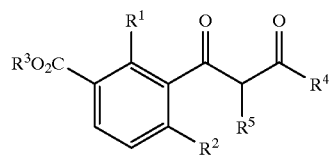

wherein $R^1$, $R^2$, $R^3$, $R^4$, and $R^5$ have the same meanings as defined above.

4. A method for the production of a compound represented by the formula [I]

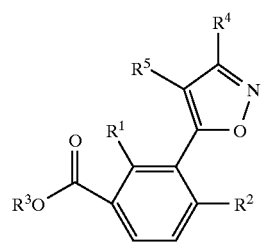

wherein $R^1$, $R^2$, $R^3$, and $R^4$, have the same meanings as defined above, comprising the steps of causing a N,N-dialkylalkyl amide alkyl acetal to react with a compound represented by the formula [V]

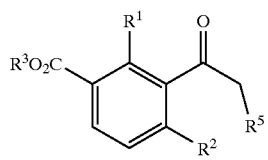

[V]

wherein $R^1$, $R^2$, $R^3$, $R^4$, and $R^5$ have the same meanings as defined above, thereby forming a compound represented by the formula [VI]

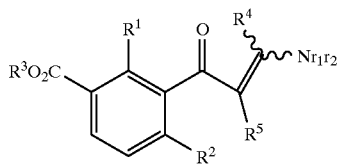

[VI]

wherein $R^1$, $R^2$, $R^3$, $R^4$, and $R^5$ have the same meanings as defined above and $r^1$ and $r^2$ each represent a $C_{1-4}$ alkyl group and then causing hydroxy amine or a hydroxy amine salt to react therewith.

5. A method for the production of a compound represented by the formula [I-5]

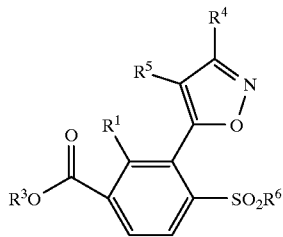

[I-5]

wherein $R^1$, $R^3$, $R^4$, and $R^5$ have the same meanings as defined above, comprising the steps of causing a mercaptan represented by $R^6SH$ to react with a compound represented by the formula [I-3]

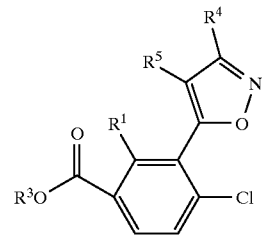

[I-3]

wherein $R^1$, $R^3$, $R^4$, and $R^5$ have the same meanings as defined above in the presence of a base thereby forming a compound represented by the formula [I-4]

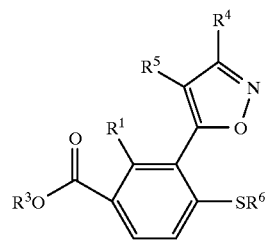

[I-4]

wherein $R^1$, $R^3$, $R^4$, and $R^5$ have the same meanings as defined above and then oxidizing said compound.

6. 2,4-Dichloro-3-(3-methyl-1,2-isooxazol-5-yl) benzoic acid.

7. 2-Chloro-3-(3-methyl-1,2-isooxazol-5-yl)-4-methyl-sulfonyl benzoic acid.

8. 2,4-Dichloro-3-(4-methyl-1,2-isooxazol-5-yl) benzoic acid.

9. 3-(3-Methyl-1,2-isooxazol-5-yl)-2-methyl-4-methyl-sulfonyl benzoic acid.

10. 3-(3-Methyl-1,2-isooxazol-5-yl)-2-methoxy-4-methyl-sulfonyl benzoic acid.

11. 4-Chloro-3-(3-methyl-1,2-isooxazol-5-yl)-2-methoxy benzoic acid.

12. 2,4-Dichloro-3-(1,2-isooxazol-5-yl) benzoic acid.

13. 4-Chloro-3-(3-methyl-1,2-isooxazol-5-yl)-2-methyl-sulfonyl benzoic acid.

14. 2-Chloro-3-(3-methyl-1,2-isooxazol-5-yl)-2-methoxy benzoic acid.

15. 2-Chloro-3-(1,2-isooxazol-5-yl)-4-methylsulfonyl benzoic acid.

* * * * *